(12) United States Patent
Rosenfeld et al.

(10) Patent No.: US 7,811,270 B2
(45) Date of Patent: *Oct. 12, 2010

(54) DISPOSABLE ABSORBENT SANITARY NAPKIN WITH MODIFIED CIRCULAR BENDING STIFFNESS AND ABSORBENCY INDEX VALUES FOR IMPROVED DRAPEABILITY

(75) Inventors: Leonard G. Rosenfeld, Yardley, PA (US); Theresa Wysocki, Flemington, NJ (US); Morris Yang, Princeton Junction, NJ (US); Marina Nikitina, New Britain, PA (US); John Poccia, Monmouth Beach, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/942,648

(22) Filed: Sep. 16, 2004

(65) Prior Publication Data

US 2006/0058753 A1 Mar. 16, 2006

(51) Int. Cl.
*A61F 13/15* (2006.01)
*A61F 13/20* (2006.01)

(52) U.S. Cl. .................. 604/385.01; 604/367; 604/374; 604/375; 604/378

(58) Field of Classification Search ..... 604/358–385.23
See application file for complete search history.

(56) References Cited

U.S. PATENT DOCUMENTS

| | | | |
|---|---|---|---|
| 4,057,061 A | 11/1977 | Ishikawa | |
| 4,357,827 A | 11/1982 | McConnell | |
| 4,555,430 A | 11/1985 | Mays | |
| 4,589,876 A | 5/1986 | Van Tilburg | |
| 4,608,047 A | 8/1986 | Mattingly | |
| 4,687,478 A | 8/1987 | Van Tilburg | |
| 4,690,679 A | 9/1987 | Mattingly, III et al. | |
| 4,900,320 A | 2/1990 | McCoy | |
| 4,950,264 A | 8/1990 | Osborn, III | |
| 4,961,930 A | 10/1990 | Perdelwitz et al. | |
| 5,009,653 A | 4/1991 | Osborn, III | |
| 5,072,687 A * | 12/1991 | Mitchell et al. ............... 118/37 |
| 5,383,869 A | 1/1995 | Osborn, III | |
| 5,437,418 A | 8/1995 | Graef et al. | |
| 5,451,219 A | 9/1995 | Suzuki et al. | |
| 5,451,437 A | 9/1995 | Insley et al. | |
| 5,509,914 A | 4/1996 | Osborn, III | |
| H1602 H | 10/1996 | Brock | |
| 5,575,786 A | 11/1996 | Osborn, III | |
| 5,601,542 A * | 2/1997 | Melius et al. ............... 604/368 |
| 5,681,300 A | 10/1997 | Ahr et al. | |
| 5,733,274 A | 3/1998 | Osborn, III | |
| 5,797,893 A * | 8/1998 | Wada et al. .................. 604/372 |
| 5,916,670 A | 6/1999 | Tan et al. | |
| 5,951,537 A | 9/1999 | Osborn, III | |
| 6,323,388 B1 * | 11/2001 | Melius et al. ............... 604/368 |
| 6,503,234 B1 * | 1/2003 | Canuel et al. .......... 604/385.01 |

(Continued)

FOREIGN PATENT DOCUMENTS

EP 0700672 A1 3/1996

(Continued)

*Primary Examiner*—Michele Kidwell

(57) ABSTRACT

An absorbent article including a cover layer, a barrier layer and an absorbent system arranged between the cover layer and the barrier layer, the absorbent article being drapeable and possessing the absorbency attributes required of a sanitary napkin.

40 Claims, 4 Drawing Sheets

U.S. PATENT DOCUMENTS

| | | |
|---|---|---|
| 6,582,411 B1 | 6/2003 | Carstens et al. |
| 6,620,143 B1 | 9/2003 | Zacharias et al. |
| 2001/0001312 A1 | 5/2001 | Mitchell et al. |
| 2001/0051795 A1* | 12/2001 | Bissah et al. ................ 604/333 |
| 2002/0007166 A1 | 1/2002 | Mitchell et al. |
| 2002/0115969 A1 | 8/2002 | Maeda et al. |
| 2003/0139718 A1 | 7/2003 | Graef et al. |
| 2004/0116014 A1 | 6/2004 | Soerens et al. |
| 2004/0138634 A1 | 7/2004 | Litvay et al. |

FOREIGN PATENT DOCUMENTS

| | | |
|---|---|---|
| EP | 0705583 | 4/1996 |
| EP | 0853934 | 7/1998 |
| EP | 1022003 A | 7/2000 |
| EP | 1078617 | 8/2000 |
| EP | 1424051 | 6/2004 |
| WO | 91/11165 | 1/1991 |
| WO | WO 95/20931 | 8/1995 |
| WO | 96/11107 A | 4/1996 |
| WO | 03/043671 A1 | 5/2003 |
| WO | WO 2004/105666 | 12/2004 |
| WO | WO 2004/112849 | 12/2004 |
| WO | 2005/044163 A1 | 5/2005 |

* cited by examiner

DISPOSABLE ABSORBENT SANITARY NAPKIN WITH MODIFIED CIRCULAR BENDING STIFFNESS AND ABSORBENCY INDEX VALUES FOR IMPROVED DRAPEABILITY

FIELD OF THE INVENTION

The present invention generally relates to sanitary absorbent articles and in particular to feminine sanitary absorbent napkins that are thin, highly absorbent and drapeable.

BACKGROUND OF THE INVENTION

Externally worn, sanitary absorbent napkins are one of many kinds of feminine protection devices currently available. The development of materials having a high liquid absorption capacity per unit volume has allowed the required overall thickness of sanitary napkins to be reduced, thereby providing a product which is more comfortable and less obtrusive to wear. Thin, flexible, sanitary napkins of this type are disclosed, for example, in U.S. Pat. No. 4,950,264 (hereinafter "the '264 patent") to T. W. Osborne III.

The term "flexible" as used in the prior art is generally used to describe an article's resistance to deformation when an external load is applied thereto. For example, the '264 patent purports to disclose a sanitary napkin having a "low flexural resistance" when an external load is applied to the sanitary napkin by means of a plunger mechanism.

However a "flexible" definition of the type provided in the '264 patent does not measure the overall "drapeable" characteristics of an absorbent article. That is, an article may have a "low flexural resistance" and yet not be "drapeable" as defined herein. The term "drapeable" or "drapeability" as used herein means the tendency of an article to hang in a vertical fashion due to gravity when held in a cantilevered manner from one end of said article. Drapeable articles also tend to conform to the shape of an abutting surface, for example a drapeable sanitary napkin will tend to conform to the body during use, thereby enhancing comfort.

Textile fabrics, and other cloth-like materials, which are used in clothing, tend to posses this "drapeable" characteristic. Clothing made from textile fabrics possessing this "drapeable" characteristic tend to conform to, and move with, to the wearer, resulting in enhanced comfort to the user.

An absorbent article possessing these "drapeable" characteristics may increase comfort to the wearer. That is, an article that is sufficiently "drapeable" such that it conforms to the space defined between the user's thighs and the user's undergarment, may increase the comfort to the wearer. In contrast, if an absorbent article is not sufficiently drapeable the wearer may experience discomfort and be conscious of the absorbent article. Additionally, if such article bunches or deforms, there is a tendency to maintain its resulting shape, thereby providing inadequate protection.

Thus, although the prior art may disclose "flexible" absorbent articles, there is still a need for absorbent articles, and in particular sanitary napkins, that are drapeable and also possess the absorbency attributes required of such absorbent articles.

SUMMARY OF THE INVENTION

The present invention is directed to an absorbent article including a cover layer; a barrier layer; an absorbent system arranged between said cover layer and said barrier layer, wherein the absorbent article includes a first portion and a second portion, wherein the absorbent article has a thickness less than 2.5 mm, the second portion having an MCB that is greater than an MCB of said first portion, and wherein at least a part of the first portion of the absorbent article satisfies one of the two following equations:

$$AI > 2.37 - 0.77 \ln(BW/MCB), \text{ where } BW/MCB \text{ is } \leq 5.9; \text{ and}$$

$$AI > 1.0; \text{ where } BW/MCB \text{ is } > 5.9.$$

In the above equations, the identified variables have the following meanings:
MCB=Modified Circular Bend Stiffness;
BW=Basis Weight of the Article; and
AI=Absorbency Index (as defined below).

BRIEF DESCRIPTION OF THE DRAWINGS

Examples of embodiments of the present invention will now be described with reference to the drawings, in which.

DETAILED DESCRIPTION OF THE INVENTION

Figure 1:
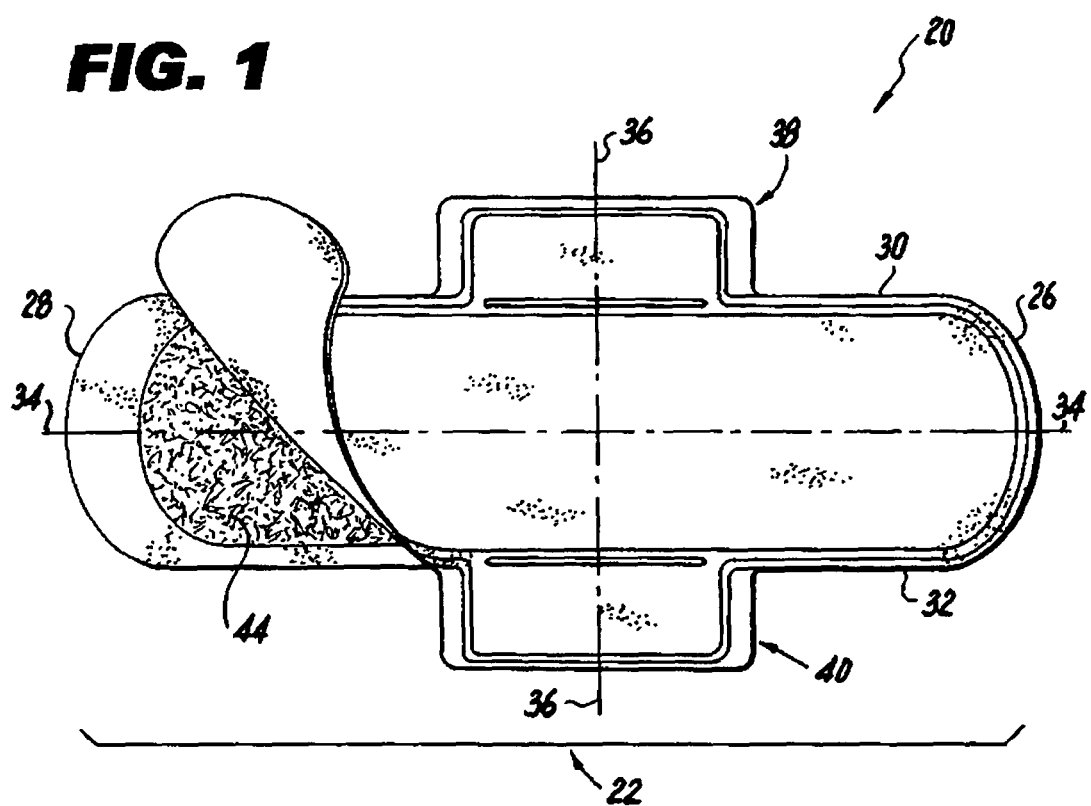
FIG. 1 is a top plan view of a sanitary napkin in accordance with an embodiment of the present invention, the cover layer of the sanitary napkin being partly removed to show the absorbent system.

Preferred embodiments of the present invention comprise absorbent articles, and in particular sanitary napkins, that are thin, flexible, drapeable and possess absorbency attributes required of sanitary napkins.

According to the present invention it has been found that a sanitary napkin that is drapeable, and possesses the absorbency attributes required of sanitary napkins, will satisfy one of the following equations:

$$AI > 2.37 - 0.77 \ln(BW/MCB), \text{ where } BW/MCB \text{ is } \leq 5.9; \text{ and}$$

$$AI > 1.0, \text{ where } BW/MCB \text{ is } > 5.9.$$

The above equations hold true where the absorbent article has a thickness of less than or equal to 2.5 mm.

In the above equations, the identified variables have the following meanings:
MCB=Modified Circular Bend Stiffness;
BW=Basis Weight of the Article; and
AI=Absorbency Index (as defined below).

The methods for calculating the above variables for a given absorbent article are described in greater detail below.

Test Procedure

To test an absorbent article according to the test method set forth herein a minimum of six samples are required. For each of the tests conducted herein, the portion of the absorbent article to tested should be the same, i.e. the test sample should be taken from corresponding locations on each of the product samples. An absorbent article satisfies the test method set forth herein if any absorbent portion of the product satisfies the test.

Procedure for Measuring Modified Circular Bend Stiffness (MCB) and Basis Weight (BW)

Modified Circular Bend Stiffness (MCB) is determined by a test that is modeled after the ASTM D 4032-82 CIRCULAR BEND PROCEDURE, the procedure being considerably modified and performed as follows. The CIRCULAR BEND PROCEDURE is a simultaneous multi-directional deformation of a material in which one face of a specimen becomes concave and the other face becomes convex. The CIRCULAR BEND PROCEDURE gives a force value related to flexural resistance, simultaneously averaging stiffness in all directions.

The apparatus necessary for the CIRCULAR BEND PROCEDURE is a modified Circular Bend Stiffness Tester, having the following parts:

1. A smooth-polished steel plate platform, which is 102.0 mm by 102.0 mm by 6.35 mm having an 18.75 mm diameter orifice. The lap edge of the orifice should be at a 45 degree angle to a depth of 4.75 mm;

2. A plunger having an overall length of 72.2 mm, a diameter of 6.25 mm, a ball nose having a radius of 2.97 mm and a needle-point extending 0.88 mm therefrom having a 0.33 mm base diameter and a point having a radius of less than 0.5 mm, the plunger being mounted concentric with the orifice and having equal clearance on all sides. Note that the needle-point is merely to prevent lateral movement of the test specimen during testing. Therefore, if the needle-point significantly adversely affects the test specimen (for example, punctures an inflatable structure), than the needle-point should not be used. The bottom of the plunger should be set well above the top of the orifice plate. From this position, the downward stroke of the ball nose is to the exact bottom of the plate orifice;

3. A force-measurement gauge and more specifically an Instron inverted compression load cell. The load cell has a load range of from about 0.0 to about 2000.0 g;

4. An actuator and more specifically the Instron Model No. 1122 having an inverted compression load cell. The Instron 1122 is made by the Instron Engineering Corporation, Canton, Mass.

In order to perform the procedure for this test, as explained below, three representative product samples for each article to be tested are necessary. The location of the sanitary napkin, or other absorbent article, to be tested is selected by the operator. A 37.5 mm by 37.5 mm test specimen is cut from each of the three product samples at corresponding locations. Prior to cutting the test specimens any release paper or packaging material is removed from the product sample and any exposed adhesive, such as garment positioning adhesive, is covered with a non-tacky powder such as talc or the like. The talc should not affect the BW and MCB measurements.

The test specimens should not be folded or bent by the test person, and the handling of specimens must be kept to a minimum and to the edges to avoid affecting flexural-resistance properties.

The procedure for the CIRCULAR BEND PROCEDURE is as follows. The specimens are conditioned by leaving them in a room that is 21° C., +/−1° C. and 50%, +/−2.0%, relative humidity for a period of two hours.

The weight of each cut test specimen is measured in grams and divided by a factor of 0.0014. This is the basis weight in units of grams per square meter (gsm). The values obtain for basis weight for each of the test specimens is averaged to provide an average basis weight (BW). This average basis weight (BW) may then be utilized in the formulas set forth above.

A test specimen is centered on the orifice platform below the plunger such that the body facing layer of the test specimen is facing the plunger and the barrier layer of the specimen is facing the platform. The plunger speed is set at 50.0 cm per minute per full stroke length. The indicator zero is checked and adjusted, if necessary. The plunger is actuated. Touching the test specimen during the testing should be avoided. The maximum force reading to the nearest gram is recorded. The above steps are repeated until all of three test specimens have been tested. An average is then taken from the three test values recorded to provide an average MCB stiffness. This average MCB value may then be used in the formulas set forth above.

The remaining non-tested product samples are then used for the Absorbency Index test set forth below.

Procedure for Determining Absorbency Index (AI)

In order for a absorbent article to function properly it must have good absorbent properties to give the user confident protection against soiling of garments and leakage. The "Absorbency Index" (AI) (as defined herein) of an absorbent article is a measure of the articles fluid handling properties. The Absorbency Index (AI) of an absorbent article is determined from composite of two fluid handling properties, Rewet (R) and Fluid Penetration Time (FPT). The Absorbency Index (AI) as used herein is defined as follows:

$$\text{Absorbency Index} = AI = \left(\frac{6.27 - R}{6.12}\right) + \left(\frac{499 - FPT}{495}\right); \text{ where}$$

R=Rewet Value

FPT=Fluid Penetration Time

The methods for determining the Rewet Value (R) and the Fluid Penetration Time (FPT) for an absorbent article are provided below. Three new product samples are required to conduct the Rewet Value (R) and Fluid Penetration Time (FPT) tests described below.

Procedure for Measuring Fluid Penetration Time

Fluid Penetration Time is measured by placing a sample to be tested under a Fluid Penetration Test orifice plate. The orifice plate consists of a 7.6 cm×25.4 cm plate of 1.3 cm thick polycarbonate with an elliptical orifice in its center. The elliptical orifice measures 3.8 cm along its major axis and 1.9 cm along its minor axis. The orifice plate is arranged on the product sample to be tested at a corresponding location on the absorbent article from which the 37 mm×37 mm test specimens were taken from the product samples tested in the MCB test described above. The longitudinal axis of the elliptical orifice is arranged parallel to the longitudinal axis of the product to be tested.

Test fluid was made of the following mixture to simulate bodily fluids: 49.5% of 0.9% sodium chloride solution (VWR catalog # VW 3257-7), 49.05% Glycerin (Emery 917), 1% Phenoxyethanol (Clariant Corporation Phenoxetol™) and 0.45% Sodium Chloride (Baker sodium chloride crystal # 9624-05).

A graduated 10 cc syringe containing 7 ml of test fluid is held over the orifice plate such that the exit of the syringe is approximately 3 inches above the orifice. The syringe is held horizontally, parallel to the surface of the test plate. The fluid is then expelled from the syringe at a rate that allows the fluid to flow in a stream vertical to the test plate into the orifice and a stop watch is started when the fluid first touches the sample to be tested. The stop watch is stopped when a portion of the surface of the sample first becomes visible above the remaining fluid within the orifice. The elapsed time on the stop watch is the Fluid Penetration Time. The average Fluid Penetration Time (FPT) is calculated from taking the average of three product samples. This average FPT in seconds may then be used in the equations set forth above.

Procedure for Measuring Rewet Potential

The three product samples used for the Fluid Penetration Time (FPT) procedure described above are used for the Rewet Potential test described below.

The rewet potential is a measure of the ability of a napkin or other article to hold liquid within its structure when the napkin contains a relatively large quantity of liquid and is subjected to external mechanical pressure. The rewet potential is determined and defined by the following procedure.

The apparatus for the Rewet Potential test is the same as that set forth above with regard to the FPT test and further includes a quantity of 3 inch×4 inch rectangles of Whatman #1 filter paper from Whatman, Inc. Clifton, N.J. and a weighing machine or balance capable of weighing to an accuracy of .+−.0.001 g, a quantity of said Whatman paper, a standard weight of 2.22 kg (4.8 pounds) having dimensions 5.1 cm (2 inches) by 10.2 cm (4.0 inches) by approximately 5.4 cm (2.13 inches) which applies a pressure of 4.14 kPa (0.6 psi) over the 5.1 by 10.2 cm (2 inches by 4 inches) surface.

For purposes of the test procedure set forth herein, the same three product samples used for the fluid penetration test should be used for the rewet potential test. After the test fluid is applied within the orifice plate in the FPT test described above, and as soon as the cover layer of the napkin first appears through the top surface of the fluid, the stop watch is started and an interval of 5 minutes is measured.

After 5 minutes have elapsed, the orifice plate is removed and the napkin is positioned on a hard level surface with the cover layer facing upwards.

A fifteen (15) layer stack of the pre-weighed filter paper is placed on and centered over the wetted area and the standard 2.22 kg weight is placed on top of the filter paper. The filter paper and the weight are arranged over the absorbent article such that they are centered over the area to which the fluid was applied. The filter paper and the weight are arranged such that their longer dimensions are aligned with the longitudinal direction of the product. Immediately after placing the paper and weight on the product, the stopwatch is started and after a 3 minute interval has elapsed the standard weight and filter paper are quickly removed. The wet weight of the filter paper is measured and recorded to the nearest 0.001 grams. The rewet value is then calculated as the difference in grams between the weight of the wet 15 layers of filter paper and the dry 15 layers of filter paper.

The measurement should have at least three replicates and, if necessary, the weight is wiped clean before each run. The average rewet value (R) in grams is then calculated from the three measured values and this rewet value (R) may then be used in the equations set forth above.

Procedure for Measuring the Thickness of a Sanitary Article

The thickness measurement procedure described below should be conducted on three product samples prior to conducting the MCB test described above after the product samples have been removed from any packaging, any release paper has been removed, and after the product has been powdered with talc or the like. The thickness measurement of the product should be conducted at the same location from which the test specimen for the MCB test will be taken.

The absorbent articles according to the present invention preferably have a thickness of less than 2.5 mm. The procedure for measuring the thickness of an absorbent article is described below.

The apparatus required to measure the thickness of the sanitary napkin is a footed dial (thickness) gauge with stand, available from Ames, with a 2" diameter foot at a pressure of 0.07 psig and a readout accurate to 0.001". A digital type apparatus is preferred. If the sanitary napkin sample is individually folded and wrapped, the sample is unwrapped and carefully flattened by hand. The release paper is removed from the product sample and it is repositioned back gently across the positioning adhesive lines so as not to compress the sample, ensuring that the release paper lies flat across the sample. Flaps (if any) are not considered when taking the thickness reading.

The foot of the gauge is raised and the product sample is placed on the anvil such that the foot of the gauge is approximately centered on the location of interest on the product sample. When lowering the foot, care must be taken to prevent the foot dropping onto the product sample or undue force being applied. A load of 0.07 p.s.i.g. is applied to the sample and the read out is allowed to stabilize for approximately 5 seconds. The thickness reading is then taken. This procedure is repeated for at least three product samples and the average thickness is then calculated.

Description of Preferred Embodiments

Figure 2:
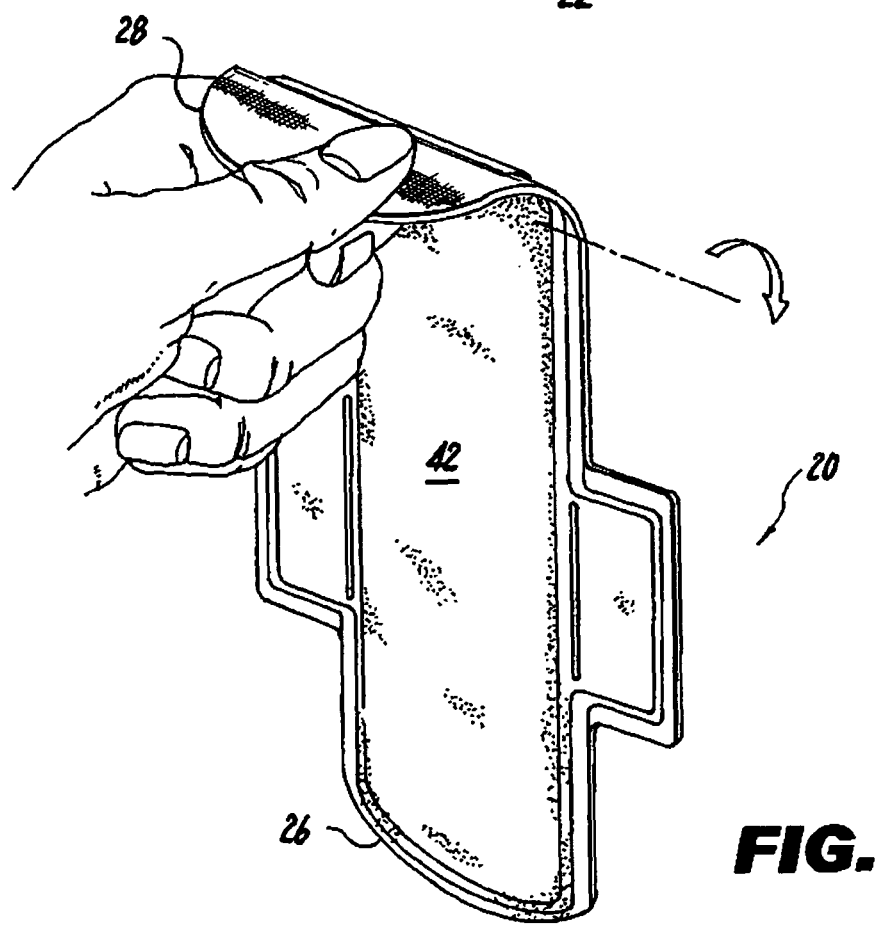
FIG. 2 is perspective view of sanitary napkin of FIG. 1, depicted in a position attained when the sanitary napkin is held in a cantilevered manner from one end of the napkin.
Figure 3:
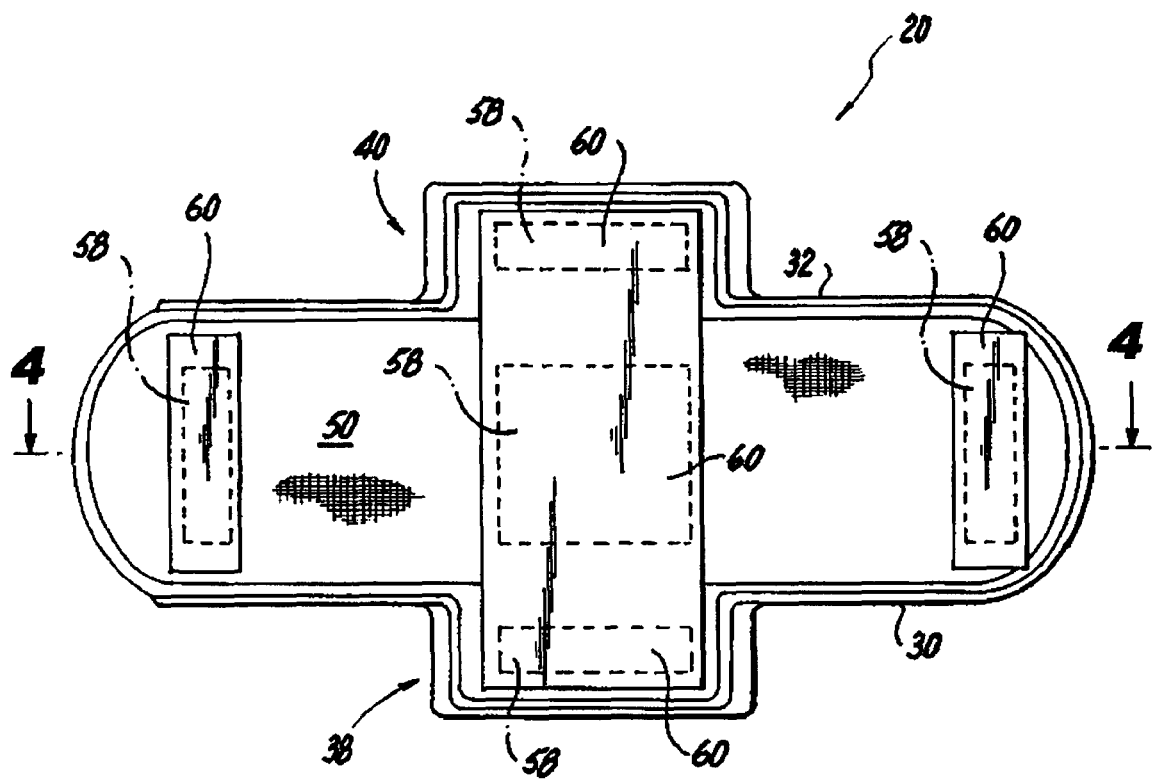
FIG. 3 is a bottom plan view of the sanitary napkin shown in FIG. 1.

Referring to FIGS. 1 and 2, there is shown an embodiment of the present invention, a feminine sanitary napkin 20.

The sanitary napkin 20 has a main body 22 with a first transverse side 26 defining a front portion thereof and a second transverse side 28 defining a rear portion thereof. The main body also has two longitudinal sides, namely a longitudinal side 30 and a longitudinal side 32. The sanitary napkin 20 preferably has a thickness not exceeding about 2.5 mm, preferably the thickness is less than 2.0 mm, more preferably less than 1.5 mm.

The sanitary napkin 20 has a longitudinal centerline 34 that is an imaginary line bisecting the sanitary napkin 20 in two identical halves. Projecting laterally outward from each of the longitudinal sides 30, 32 is a flap 38 and 40 respectively. The main body 22 also has an imaginary transverse centerline 36 perpendicular to the longitudinal centerline 34 and simultaneously bisecting the flaps 38, 40.

Figure 4:
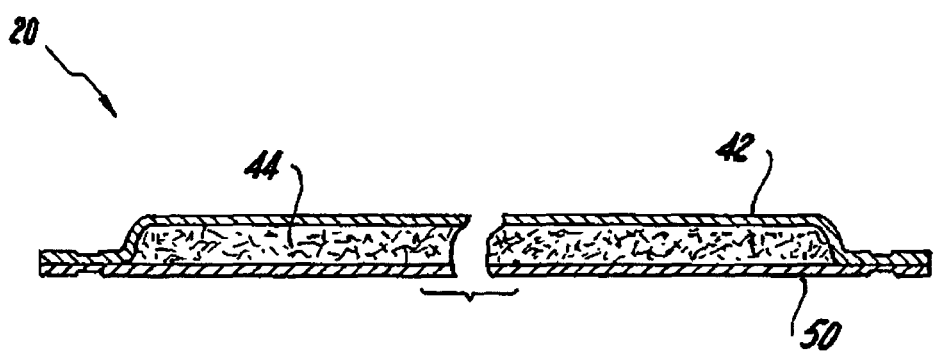
FIG. 4 is a cross sectional view taken along the longitudinal center line 4-4 of the sanitary napkin shown in FIG. 3.

As depicted in FIG. 4, the main body 22 is of a laminate construction and preferably comprises a fluid-permeable cover layer 42, an absorbent system 44 and a fluid-impervious barrier layer 50. The absorbent system 44 may comprise a single layer of material or may comprise multiple layers. For example the absorbent system may comprise a single layer core or it may include a transfer layer and a core.

Main Body—Cover Layer

The cover layer 42 may be a relatively low density, bulky, high-loft non-woven web material. The cover layer 42 may be composed of only one type of fiber, such as polyester or polypropylene or it may include a mixture of more than one fiber. The cover may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof. Preferably, the cover layer 42 has a basis weight in the range of about 10 gsm to about 75 gsm.

Bi-component fibers may be made up of a polyester layer and a an polyethylene sheath. The use of appropriate bi-component materials results in a fusible non-woven fabric. Examples of such fusible fabrics are described in U.S. Pat. No. 4,555,430 issued Nov. 26, 1985 to Chicopee. Using a fusible fabric increases the ease with which the cover layer may be mounted to the absorbent layer and/or to the barrier layer.

The cover layer 42 preferably has a relatively high degree of wettability, although the individual fibers comprising the cover may not be particularly hydrophilic. The cover material should also contain a great number of relatively large pores. This is because the cover layer 42 is intended to take-up body fluid rapidly and transport it away from the body and the point of deposition. Therefore, the cover layer contributes little to the time taken for the napkin to absorb a given quantity of liquid (penetration time).

Advantageously, the fibers which make up the cover layer 42 should not lose their physical properties when they are wetted, in other words they should not collapse or lose their resiliency when subjected to water or body fluid. The cover layer 42 may be treated to allow fluid to pass through it readily. The cover layer 42 also functions to transfer the fluid quickly to the other layers of the absorbent system 44. Thus, the cover layer 42 is advantageously wettable, hydrophilic and porous. When composed of synthetic hydrophobic fibers such as polyester or bi-component fibers, the cover layer 42 may be treated with a surfactant to impart the desired degree of wettability.

In one preferred embodiment of the present invention the cover is made from a spunlace nonwoven material having from about 0 to about 100% polyester and from about 0 to about 100% rayon. The spunlace material may also be made from about 10% to about 65% rayon and from about 35% to about 90% polyester. In lieu of, and/or in combination with the polyester, polyethylene, polypropylene or cellulosic fiber may be used with the rayon. Optionally, the material used for the cover layer may include binders such as thermoplastic binders and latex binders.

Alternatively, the cover layer 42 can also be made of polymer film having large pores. Because of such high porosity, the film accomplishes the function of quickly transferring body fluid to the inner layers of the absorbent system. Apertured co-extruded films such described in U.S. Pat. No. 4,690,679 and available on sanitary napkins sold by Johnson & Johnson Inc. of Montreal, Canada could be useful as cover layers in the present invention.

The cover layer 42 may be embossed to the remainder of the absorbent system 44 in order to aid in promoting hydrophilicity by fusing the cover to the next layer. Such fusion may be effected locally, at a plurality of sites or over the entire contact surface of cover layer 42 and absorbent system 44. Alternatively, the cover layer 42 may be attached to the absorbent system 44 by other means such as by adhesion.

Main Body—Absorbent System

The absorbent system 44 may comprise a single layer of material or may comprise multiple layers. In one embodiment, the absorbent system 44 is a blend or mixture of cellulosic fibers and superabsorbent disposed in and amongst fibers of that pulp.

It is possible that the absorbent system 44 could be integrated with the cover and/or barrier such that there is essentially only a single layer structure or a two layer structure including the function of the multiple layers described herein.

Cellulosic fibers that can be used in the absorbent system 44 are well known in the art and include wood pulp, cotton, flax and peat moss. Wood pulp is preferred. Pulps can be obtained from mechanical or chemi-mechanical, sulfite, kraft, pulping reject materials, organic solvent pulps, etc. Both softwood and hardwood species are useful. Softwood pulps are preferred. It is not necessary to treat cellulosic fibers with chemical debonding agents, cross-linking agents and the like for use in the present material. Some portion of the pulp may be chemically treated as discussed in U.S. Pat. No. 5,916,670 to improved flexibility of the product. Flexibility of the material may also be improved by mechanically working the material or tenderizing the material. The absorbent system 44 can contain any superabsorbent polymer (SAP), which SAPs are well known in the art. For the purposes of the present invention, the term "superabsorbent polymer" (or "SAP") refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Preferred superabsorbent polymer particles for use in the present invention are crosslinked polyacrylates, such as the product offered by Sumitomo Seika Chemicals Co., Ltd. Of Osaka, Japan, under the designation of SA70N and products offered by Stockhausen Inc.

In a specific example, the absorbent system 44 is a material containing from 90% to about 40% percent cellulosic fiber, about 10% to about 60% SAP and is substantially free of binder materials such as latex materials. This material preferably is selectively embossed so that it has regions of relatively higher and lower densities. In particular, the material is preferably embossed to have a first region having a density greater than a density of a second region wherein said first region comprises between about 20% to about 60% of the surface area of the material and wherein the second region comprises between about 40% to about 80% of the surface area of the material. Preferably, the first region has a density greater than 0.3 g/cc and the second region has a density in the range from about 0.07 to 0.25 g/cc. The material preferably has a basis weight of about 50 gsm to about 600 gsm. The material may also include a carrier layer on either surface of the material.

The absorbent system 44 may comprise a material manufactured by using air-laying means well known in the art. In a specific example, the absorbent system 44 is an air laid material made from cellulosic fibers, binder material and components that cannot form a bond (nonbonding materials) with the other component materials. The binder material may comprise a latex binder, thermoplastic particles or fibers, adhesives or bicomponent fibers and the nonbonding materials may comprise SAP and/or synthetic fibers that will not melt and bond at the process temperatures. Preferably, the material includes less than 50% cellulosic fibers, less than 20% binder material and greater 30% nonbonding materials. The material also preferably has a basis weight in the range of about 50 gsm to about 600 gsm and a density in the range of about 0.03 g/cc to about 0.2 g/cc.

In another specific example, the absorbent system 44 is composed from only SAP powder deposited between the cover and barrier. Typical pressure sensitive adhesives such as Fuller 1491 available from the Fuller Corporation can be coated to the internal surface of the barrier to hold the SAP powder in place. SAP's with very rapid absorbency rates such as Sumitomo J550 (Sumitomo Seika Chemical Companies Ltd., Osaka, Japan) have been found to be particularly well suited. For this construction, the SAP layer is preferably substantially uniform with a basis weight of at least 50 gsm and preferably between 100 and 150 gsm.

Suitable types of SAP for this SAP only embodiment have an absorbency of at least 20 g/g after 1 minute ("the absorbency rate") and a total capacity of at least 40 g/g ("the total capacity"). This value is based upon an absorption of 0.9% saline solution in a GAT (Gravimetric Absorbency Tester) device under a pressure of 0.01 psi. A detailed description of a GAT apparatus is described by McConnell in U.S. Pat. No. 4,357,827, the subject matter of which is hereby incorporated by reference. GAT systems are available from M/K Systems, Danners, Mass. A detailed description of the test method used to determine absorbency values of the SAP set forth above is provided below.

SAP was prepared for the test by first screening out the SAP using a 100-mesh screen to isolate SAP that would remain on top of a 100-mesh screen.

The test cell of the GAT apparatus is adjusted such that is 1 cm above the level of the fluid reservoir. Whatman GF/A filter paper was placed on top of the test cell of the GAT apparatus, the test cell comprising a multi-hole plate. The filter paper functions insure that a continuous flow of test fluid is delivered to the SAP.

A test chamber was constructed from a 1-inch ID plexiglass tube having a first open end and a second end covered by a 100-mesh metal screen. An amount of 0.10 gram SAP powder was placed in the test chamber on top of the metal screen, this amount of SAP corresponding to 200 gsm. A 4.4 gram plexiglass puck machined to closely fit within, but not bind the cylinder, was placed on top of the powder to provide a nominal load of 0.01 psi.

The test chamber was placed on top of the filter paper so the outer surface of the screen is in abutment with the filter paper arranged on the GAT test cell. The test was run over 60 minutes, data on the amount of fluid absorbed was captured ever 15 seconds by a computer. For the SAP sample, an absorbency curve was generated by plotting g/g capacity v. time. The "absorbency rate" as used herein was the amount of fluid absorbed after 1 minute on a gram per gram basis and the "total capacity" as used herein was the amount of fluid absorbed after 60 minutes on a gram per gram basis.

A second test, as described above, was conduct on the same type of SAP used in the above test. However, in this second test an amount of 0.50 gram SAP powder was placed in the test chamber on top of the metal screen, this amount of SAP corresponding to 1000 gsm. The second test in all other respects were carried out as described above and a second absorbency curve was generated by plotting g/g capacity v. time.

The total capacity measured from the 0.10 gram SAP test (i.e. the first test) and the total capacity measured from the 0.50 gram SAP test (i.e. the second test) were compared. A "gel blocking ratio" was determined from the ratio of the total capacity of the 0.50 gram sample on a gram per gram basis relative to the total capacity of the 0.10 gram sample on a gram per gram basis. SAP's useful in the present invention will have a "gel blocking ratio" of at least 0.50.

It is possible that the absorbent system 44 could be integrated with the cover and/or barrier such that there is essentially only a single layer structure or a two layer structure including the function of the multiple layers described herein.

Main Body—Barrier Layer

Underlying the absorbent layer 44 is a barrier layer 50 comprising liquid-impervious film material so as to prevent liquid that is entrapped in the absorbent system 44 from egressing the sanitary napkin and staining the wearer's undergarment. The barrier layer 50 is preferably made of polymeric film, although it may be made of liquid impervious, air-permeable material such as repellent-treated non-woven or micropore films or foams.

Positioning adhesive 58 may be applied to a garment facing side of the barrier layer for securing the napkin 20 to the garment during use. The positioning adhesive 58 may be covered with removable release paper 60 so that the positioning adhesive is covered by the removable release paper 60 prior to use.

The barrier layer may be breathable, i.e., permits vapor to transpire. Known materials for this purpose include non-woven materials and microporous films in which microporosity is created by, inter alia, stretching an oriented film. Single or multiple layers of permeable films, fabrics, melt-blown materials, and combinations thereof that provide a tortuous path, and/or whose surface characteristics provide a liquid surface repellent to the penetration of liquids may also be used to provide a breathable backsheet. The cover layer 42 and the barrier layer 50 are joined along their marginal portions so as to form an enclosure or flange seal that maintains the absorbent layer 44 captive. The joint may be made by means of adhesives, heat-bonding, ultrasonic bonding, radio frequency sealing, mechanical crimping, and the like and combinations thereof.

Main Body—Stabilizing Layer

Figure 5:
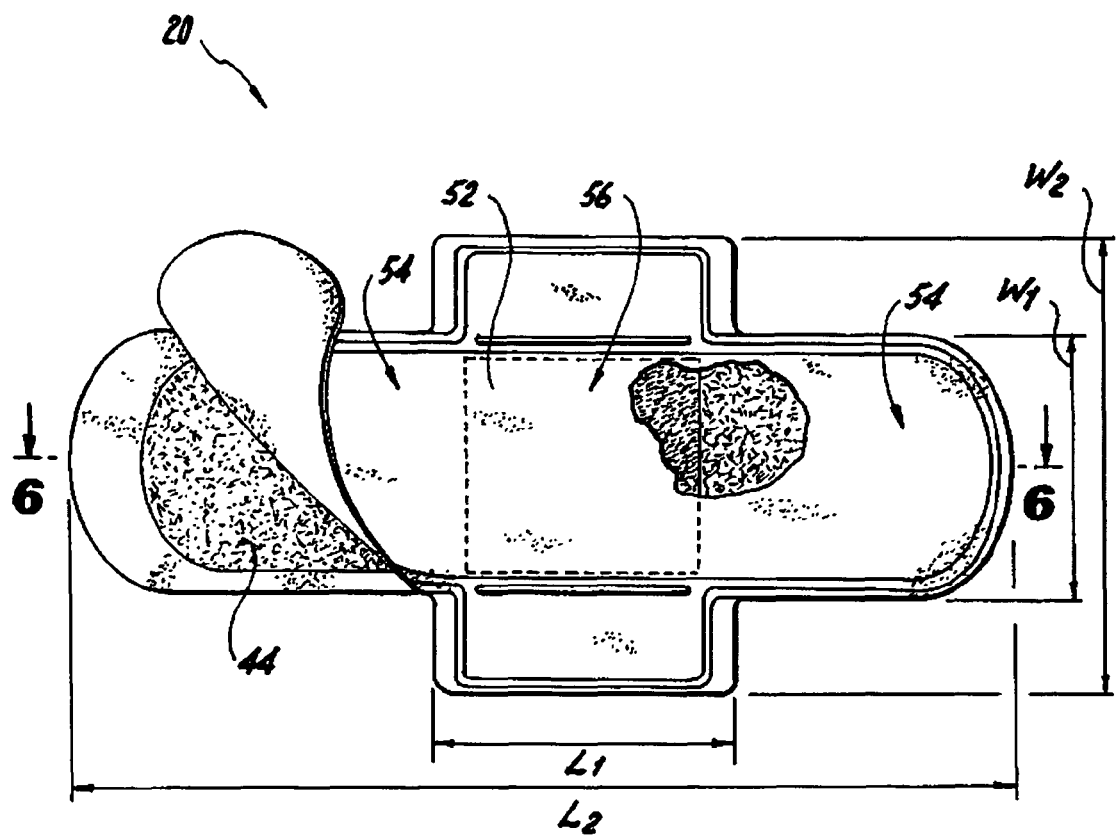
FIG. 5 is a top plan view of a sanitary napkin in accordance with another embodiment of the present invention the cover layer of the sanitary napkin being partly removed to show the absorbent system.
Figure 6:
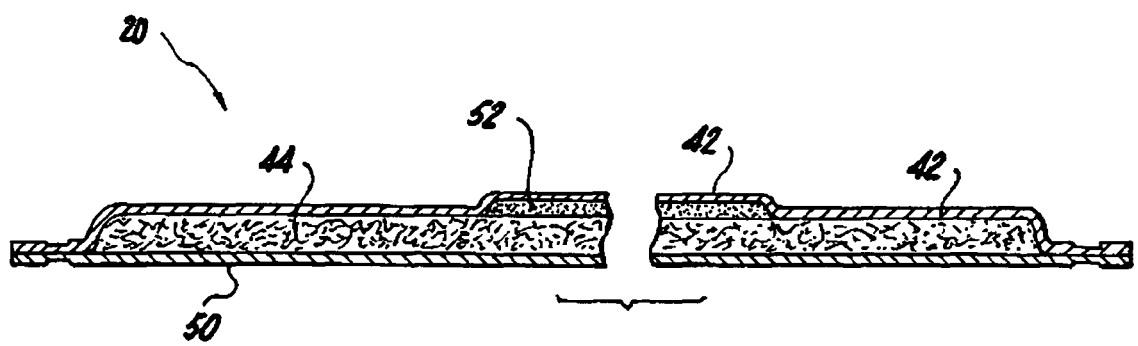
FIG. 6 is a cross sectional view taken along the longitudinal center line 6-6 of the sanitary napkin shown in FIG. 5.

As shown in FIGS. 5 and 6, the sanitary napkin 20 may further optionally include a stabilizing layer 52 arranged between the cover layer 42 and the barrier 50. The stabilizing layer 52 may be arranged between the absorbent system 44 and the cover layer 42 or it may be arranged between the absorbent system 44 and the barrier 50. The stabilizing layer 52 is intended to provided the napkin with a higher flexural resistance (MCB) in a localized area. The stabilizing layer 52 is intended to enhance the structural integrity of the napkin 20 in a localized area while at the same time still permitting the overall nature of the napkin to be "drapeable".

The stabilizing layer 52 preferably has a length L1 that is less than a length L2 of the absorbent system 44. In this manner, the napkin generally has a first portion 54 that is located outside the dimensions of the stabilizing layer 52 and a second portion 56 located within the dimensions of the stabilizing layer 52. The material for the stabilizing layer 52 is selected such that the napkin 20 has a flexural resistance (MCB) that is greater within the dimensions of the stabilizing layer 52, i.e. within second portion 56, than outside the dimensions of the stabilizing layer 52, i.e. within the first portion 54.

Thus, the napkin will have at least a first MCB value outside the dimensions of the stabilizing 52 and a second MCB value within the dimensions of the stabilizing layer 52, the first MCB value being less than the second MCB value. Preferably the second MCB value is at least 400 g. The MCB values of the first portion 54 and the second portion 56 may be calculated in the same manner set forth in the "Procedure for Measuring Modified Circular Bend Stiffness (MCB) and Basis Weight (BW)" set forth above.

The width W1 of the stabilizing layer 52 is preferably selected such that it is the same as the width W2 of the absorbent system 44. Preferably the stabilizing layer has a length L1 of at least 37.5 mm and width W1 of at least 37.5 mm.

If the stabilizing layer 52 is arranged between the cover layer 42 and the absorbent system 44, the material comprising the stabilizing layer 52 should be selected such that it readily transmits fluid to the absorbent system 44. For example, the stabilizing layer 52 may comprise a nonwoven material including a blend or mixture of synthetic and/or cellulosic fibers. Suitable specific material compositions will be apparent to those skilled in the art.

If the stabilizing layer 52 is arranged between the absorbent system 44 and the barrier 50, the material comprising the stabilizing layer may be liquid impermeable. In this manner, the stabilizing layer 52 may assist the barrier 50 in preventing fluid from escaping from the absorbent article.

Alternatively, if the stabilizing layer is arranged between the absorbent system 44 and the barrier 50, the material comprising the stabilizing layer may be absorbent such that it functions as a secondary core. For example, the stabilizing layer 52 may comprise a nonwoven material including a blend or mixture of cellulosic fibers and SAP.

Finally, the stabilizing layer 52 may be arranged on the outer surface of the barrier. In such an embodiment the material comprising the stabilizing layer is preferably liquid impermeable and thus functions as a secondary barrier.

Absorbent articles of this invention may or may not include wings, flaps or tabs for securing the absorbent article to an undergarment. Wings, also called, among other things, flaps or tabs, and their use in sanitary protection articles is described in U.S. Pat. No. 4,687,478 to Van Tilburg; U.S. Pat. No. 4,589,876 also to Van Tilburg, U.S. Pat. No. 4,900,320 to McCoy, and U.S. Pat. No. 4,608,047 to Mattingly. The disclosures of these patents are incorporated herein by reference in their entirety. As disclosed in the above documents, wings are generally speaking flexible and configured to be folded over the edges of the underwear so that the wings are disposed between the edges of the underwear.

The absorbent article of the present invention may be applied to the crotch by placing the garment-facing surface against the inside surface of the crotch of the garment. Various methods of attaching absorbent articles may be used. For example, chemical means, e.g., adhesive, and mechanical attachment means, e.g., clips, laces, ties, and interlocking devices, e.g., snaps, buttons, VELCRO (Velcro USA, Inc., Manchester, N.H.), zipper, and the like are examples of the various options available to the artisan.

Adhesive may include pressure sensitive adhesive that is applied as strips, swirls, or waves, and the like. As used herein, the term pressure-sensitive adhesive refers to any releasable adhesive or releasable tenacious means. Suitable adhesive compositions, include, for example, water-based pressure-sensitive adhesives such as acrylate adhesives. Alternatively, the adhesive composition may include adhesives based on the following: emulsion or solvent-borne adhesives of natural or synthetic polyisoprene, styrene-butadiene, or polyacrylate, vinyl acetate copolymer or combinations thereof; hot melt adhesives based on suitable block copoylmers—suitable block copolymers for use in the invention include linear or radial co-polymer structures having the formula (A-B)x wherein block A is a polyvinylarene block, block B is a poly(monoalkenyl) block, x denotes the number of polymeric arms, and wherein x is an integer greater than or equal to one. Suitable block A polyvinylarenes include, but are not limited to Polystyrene, Polyalpha-methylstyrene, Polyvinyltoluene, and combinations thereof. Suitable Block B poly(monoalkenyl) blocks include, but are not limited to conjugated diene elastomers such as for example polybutadiene or polyisoprene or hydrogenated elastomers such as ethylene butylene or ethylene propylene or polyisobutylene, or combinations thereof. Commercial examples of these types of block copolymers include Kraton™ elastomers from Shell Chemical Company, Vector™ elastomers from Dexco, Solprene™ from Enichem Elastomers and Stereon™ from Firestone Tire & Rubber Co.; hot melt adhesive based on olefin polymers and copolymers where in the olefin polymer is a terpolymer of ethylene and a co-monomers, such as vinyl acetate, acrylic acid, methacrylic acid, ethyl acrylate, methyl acrylate, n-butyl acrylate vinyl silane or maleic anhydride. Commercial examples of these types of polymers include Ateva(polymers from AT plastics), Nucrel(polymers from DuPont), Escor (from Exxon Chemical).

Where adhesive is used, a release strip may be applied to protect the adhesive on the absorbent article prior to attaching the absorbent article to the crotch. The release strip can be formed from any suitable sheet-like material adheres with sufficient tenacity to the adhesive to remain in place prior to use but which can be readily removed when the absorbent article is to be used. Optionally, a coating may be applied to release strip to improve the ease of removability of the release strip from the adhesive. Any coating capable of achieving this result may be used, e.g., silicone.

Any or all of the cover, absorbent layer, transfer layer, backsheet layer, and adhesive layers may be colored. Such coloring includes, but is not limited to, white, black, red, yellow, blue, orange, green, violet, and mixtures thereof. Color may be imparted according to the present invention through dying, pigmentation, and printing. Colorants used according the present invention include dyes and inorganic and organic pigments. The dyes include, but are not limited to, anthraquinone dyes (Solvent Red 111, Disperse Violet 1, Solvent Blue 56, and Solvent Green 3), Xanthene dyes (Solvent Green 4, Acid Red 52, Basic Red 1, and Solvent Orange 63), azine dyes (Jet black), and the like. Inorganic pigments include, but are not limited to, titanium dioxide (white), carbon black (black), iron oxides (red, yellow, and brown), chromium oxide (green), ferric ammonium ferrocyanide (blue), and the like.

Organic pigments include, but are not limited to diarylide yellow AAOA (Pigment Yellow 12), diarylide yellow AAOT (Pigment Yellow 14), phthalocyanine blue (Pigment Blue 15), lithol red (Pigment Red 49:1), Red Lake C (Pigment Red), and the like.

The absorbent article may include other known materials, layers, and additives, such as, foam, net-like material, perfumes, medicaments or pharmaceutical agents, moisturizers, odor control agents, and the like. The absorbent article can optionally be embossed with decorative designs.

The absorbent article may be packaged as unwrapped absorbent articles within a carton, box or bag. The consumer withdraws the ready-to-use article as needed. The absorbent article may also be individually packaged (each absorbent article encased within an overwrap).

Also contemplated herein include asymmetrical and symmetrical absorbent articles having parallel longitudinal edges, dog bone- or peanut-shaped, as well as articles having a tapered construction for use with thong-style undergarments.

From the foregoing description, one skilled in the art can ascertain the essential characteristics of this invention, and without departing from the spirit and scope thereof, can make various changes and modifications. Embodiments set forth by way of illustration are not intended as limitations on the variations possible in practicing the present invention.

Inventive Samples

Inventive Sample 1 having a two layer spunlace nonwoven cover which has a top body facing layer of 56 gsm of PET fibers and a bottom rayon layer which is 19 gsm. The absorbent layer that is directly underneath the cover consists of wetlaid tissue carriers (17 grams per square meter basis weight, produced by Cellu Tissue Holdings Inc., East Hartford Conn.) on both faces with a mixture of wood pulp, polyester fibers and Sumitomo SA70 SAP disposed between the layers. The pulp is bleached softwood pulp, produced by a kraft process. Approximately 20% of the pulp has been mercerized. The total composite has a basis weight of 250 gsm and contains 40% superabsorbent (Sumitomo SA70) and 6% polyester staple fibers (3.0 DPF by 1.5"inch cut length, KOSA #611153, Salisbury, N.C.). The airlaid machine which produces this material consists of unwinds, hammermills, air-laid forming heads, SAP dispensers, and a heated calendering station with a pattern roll and a flat anvil roll. Fluff pulp mixed with SAP and PET fibers in the air-laid forming chambers is cast on the first carrier tissue with a strong vacuum underneath. Before the composite reaches the calendering station another tissue is introduced from the top. It is then calender between the flat anvil roll and the patterned calendar roll. The calendar roll pattern consists of a matrix of diamonds with lines between the diamonds raised to a height of 0.075". The diamonds have a major axis of 0.325" and a minor axis of 0.201". The diamonds have a spacing of 0.046" between them. After the heat emboss calendering, the embossed area between the diamonds had a density of about 0.4 g/cc and the diamond shaped raised area has density of 0.15 g/cc. The barrier film, below the absorbent layer is a 0.9 mil polyethylene film produced by Pliant Corp, Pliant # 3492A. The absorbent facing surface of the barrier had 5.9 mg/sq in of Fuller 1023 adhesive applied to it to hold the product together. The absorbent facing surface of the cover had 2.6 mg/sq in of Fuller 1023 adhesive. The garment facing surface of the barrier was coated with 20 mg/sq inch of a pressure sensitive adhesive intended for panty attachment, Fuller 1417.

Inventive Sample 2 having a two layer spunlace nonwoven cover which has a top body facing layer of 56 gsm of PET fibers and a bottom rayon layer which is 19 gsm. The absorbent layer that is directly underneath the cover consists of wetlaid tissue carriers (17 grams per square meter basis weight, produced by Cellu Tissue Holdings Inc., East Hartford Conn.) on both faces with a mixture of wood pulp, polyester fibers and Sumitomo SA70 SAP disposed between the layers. The pulp is bleached softwood pulp, produced by a kraft process. Approximately 20% of the pulp has been mercerized. The total composite has a basis weight of 175 gsm and contains 40% superabsorbent (Sumitomo SA70). The airlaid machine which produces this material consists of unwinds, hammermills, air-laid forming heads, SAP dispensers, and a heated calendering station with a pattern roll and a flat anvil roll. Fluff pulp mixed with SAP in the air-laid forming chambers is cast on the first carrier tissue with a strong vacuum underneath. Before the composite reaches the calendering station another tissue is introduced from the top. It is then calender between the flat anvil roll and the patterned calendar roll. The calendar roll pattern consists of a matrix of diamonds with lines between the diamonds raised to a height of 0.075". The diamonds have a major axis of 0.325" and a minor axis of 0.201". The diamonds have a spacing of 0.046" between them. After the heat emboss calendering, the embossed area between the diamonds had a density of about 0.4 g/cc and the diamond shaped raised area has density of 0.15 g/cc. The barrier film, below the absorbent layer is a 0.9 mil polyethylene film produced by Pliant Corp, Pliant # 3492A. The absorbent facing surface of the barrier had 5.9 mg/sq in of Fuller 1023 adhesive applied to it to hold the product together. The absorbent facing surface of the cover had 2.6 mg/sq in of Fuller 1023 adhesive. The garment facing surface of the barrier was coated with 20 mg/sq inch of a pressure sensitive adhesive intended for panty attachment, Fuller 1417.

Inventive Sample 3 having a barrier layer of 0.9 mil polyethylene film produced by Pliant Corp, #3492A with 5.9 mg/sq in of Fuller 1023 adhesive applied to the cover facing surface of the barrier layer. 1.2 grams of Sumitomo J550 superabsorbent polymer powder was evenly sprinkled onto a 50 mm by 172 mm rectangle in the center of the barrier film so that the SAP powder was help in place by the adhesive. A 30 gsm thermal bonded polypropylene cover (Code #65130 available from Polymer Group Inc. Charleston, S.C.) was placed on top of the SAP and barrier film. The cover had 2.6 mg/sq in of Fuller 1023 adhesive on the SAP facing side to bond it to the SAP and the barrier film. The cover an barrier films extended about 10 mm beyond the SAP containing region and were secured to each other. The garment facing surface of the barrier was coated with 20 mg/sq inch of a pressure sensitive adhesive intended for panty attachment, Fuller 1417.

Inventive Sample 4 having a cover layer of 50 gsm spunlaced polypropylene/polyester a core of 70 gsm (excluding carrier) through air bonded airlaid pulp and a barrier of 0.7 mil polypropylene film from Pliant, code X3471A. The core is a 70 gsm airlaid (excluding carrier) containing 6% KoSa 6dpf polyester fiber, 14.6% Treveria Type 255 3dpf bicomponent fiber, 46.5% wood pulp fibers, 28.6% SAP Sumitomo Seika, Osaka, Japan and 4.3% Vinamul Polymers A Unit of National Starch and Chemical Company Bridgewater, N.J. latex binder Code 4401 with a Tg of −23 C. The airlaid components are cast onto a 17-gsm-tissue carrier. The cover had 2.6 mg/sq.in of Fuller 1023 on the absorbent facing side and the barrier had 5.9 mg/sq in of Fuller 1023 on the absorbent facing side. The garment-facing surface of the barrier was coated with 20 mg/sq inch of a pressure sensitive adhesive intended for panty attachment, Fuller 1417.

Comparative Sample #1 Carefree Perfect Fit Pantiliner
Comparative Sample #2 Kotex Lightdays Pantiliner
Comparative Sample #3 Always Ultrathin Sanitary Napkin
Comparative Sample #4 Stayfree Ultrathin Overnight Sanitary Napkin
Comparative Sample #5 Libra Invisible Sanitary Napkin (Australia)
Comparative Sample #6 Carefree Ultra Dry Pantiliner The inventive samples and comparative samples set forth above were tested according to the test method set forth herein, the results of which are set forth in the table provided below.

|  | Basis Weight (gsm) | MCB (g) | Thickness (mm) | BW/MCB (1/m²) | Rewet (g) | FPT (s) | AI |
|---|---|---|---|---|---|---|---|
| Inventive Sample 1 | 419 | 101 | 2.3 | 4.15 | 1.75 | 17.91 | 1.71 |
| Inventive Sample 2 | 330 | 114 | 1.7 | 2.89 | 1.28 | 41.16 | 1.74 |
| Inventive Sample 3 | 256 | 12.1 | 1.2 | 21.16 | .41 | 93.44 | 1.78 |
| Inventive Sample 4 | 260 | 62 | 1.43 | 4.19 | 4.38 | 24.35 | 1.27 |
| Comparative Sample 1 | 116 | 20 | .85 | 5.80 | 6.27 | 499.88 | 0 |
| Comparative Sample 2 | 234.66 | 131.28 | 2.0 | 1.79 | 5.575 | 17.96 | 1.09 |
| Comparative Sample 3 | 292 | 247 | 2.55 | 1.18 | .05 | 5.8 | 2.0 |
| Comparative Sample 4 | 306 | 433 | 2.69 | .71 | .15 | 4.96 | 2.0 |
| Comparative Sample 5 | 569 | 475 | 3.01 | 1.2 | .307 | 5.55 | 1.97 |
| Comparative Sample 6 | 351 | 112 | 3.32 | 3.13 | 1.21 | 7.1 | 1.82 |

Figure 7:
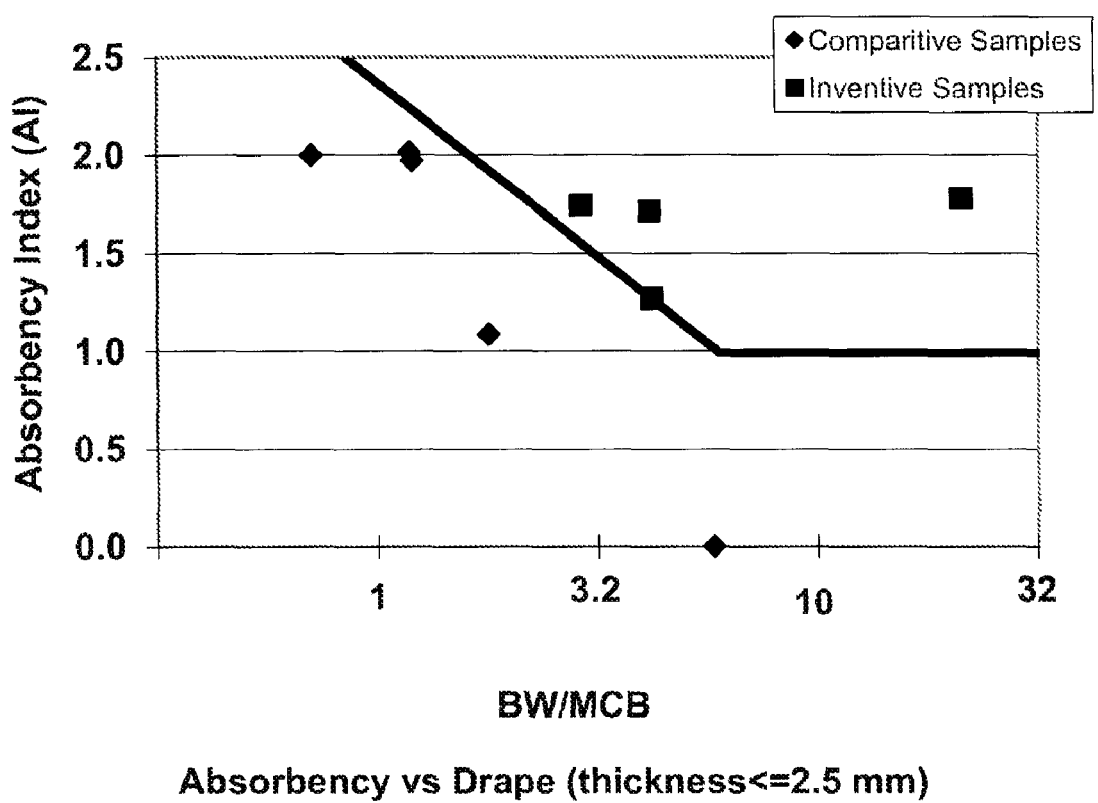
FIG. 7 is a graph plotting Absorbency Index (AI) versus BW/MCB for product examples in accordance with the present invention as well as comparative product examples.

Products set forth in the above chart having a thickness less than 2.5 mm and satisfying one of the two following equations:

$$AI > 2.37 - 0.77 \ln(BW/MCB), \text{ where } BW/MCB \text{ is} \leq 5.9; \text{ and}$$

$$AI > 1.0, \text{ where } BW/MCB \text{ is} > 5.9.$$

are shown in the graph depicted in FIG. 7. The comparative samples are also shown on the graph for comparison.

Procedure for Measuring Average Absorbent Capacity (AC)

Each of the inventive sample products 1-4 and comparative sample products 1-6 were further tested to determine the average absorbent capacity (AC) of the products. The test method for determining the average absorbent capacity (AC) is set forth below.

At least three new product samples, are required to the conduct the average absorbent capacity test described below.

The average absorbent capacity test is conducted on 37.5 mm×37.5 mm square test specimens cut from the product sample. The cut square 37.5 mm×37.5 mm test specimens are taken from the corresponding product locations as those samples taken from the products used in the MCB and AI tests described above.

Prior to doing the test, at least six 60 mm×60 mm square envelopes are constructed from a lightweight nonwoven such as 0.7 ounce per sq yard through air bonded web of bicomponent fibers. A suitable example of the nonwoven material is PGI code # 4128. The envelope can be formed by folding a 120 mm×60 mm square section and heat sealing the sides with the sample enclosed. Other envelope constructions can be use as long as they permit unhindered absorption of the test fluid to the sample during the submergence portion of the test and unhindered dripping during the dripping portion.

An envelope, without the test specimen, is submerged in a saline solution (0.9%) for 15 minutes, and then hung so that saline can freely drip for 12 minutes. The wet weight of the envelope is then measured to the nearest one hundredth of a gram. This procedure is conducted for three envelope samples and the average wet weight of the envelope is determined.

The weight of each of the three dry 37.5 mm×37.5 mm test specimens is measured before beginning the test.

A 37.5 mm×37.5 mm test specimen is inserted in an dry envelope and the envelope is submerged in a saline solution (0.9%) for 15 minutes and then hung so that saline can freely drip for 12 minutes. The wet weight of the combined envelope and test specimen are then measured to the nearest one hundredth of a gram. The dry weight of the test specimen and the average wet weight of the envelope alone are then subtracted to determine the absorbent capacity of the test specimen. This is repeated for three 37.5 mm×37.5 mm test specimens and the absorbent capacity average is taken to provide the average absorbent capacity (AC). A chart is provided below which provides the average absorbent capacity (AC) for each of the inventive sample products 1-4 and comparative sample products 1-6.

|  | Absorbent Capacity (g) (AC) |
|---|---|
| Inventive Sample 1 | 12.24 |
| Inventive Sample 2 | 9.52 |
| Inventive Sample 3 | 10.61 |
| Inventive Sample 4 | 4.82 |
| Comparative Sample 1 | .95 |
| Comparative Sample 2 | 2.67 |
| Comparative Sample 3 | 5.32 |
| Comparative Sample 4 | 9.63 |
| Comparative Sample 5 | 8.44 |
| Comparative Sample 6 | 11.32 |

Each of the inventive samples described above were constructed without a stabilizing layer 52 as described above with reference to FIGS. 5 and 6. However, each of the inventive samples described above could be constructed to include such a stabilizing layer 52. For example, inventive sample 5 described in detail below was constructed to include a stabilizing layer 52.

Inventive Sample 5

Inventive sample 5 had the same construction as inventive sample 2 described above but further included a stabilizing layer arranged between the barrier and the absorbent layer. The stabilizing layer was constructed from 102 gsm spunbond polypropylene, commercially available from BBA Fiberweb Filtration as Typar/Tekton Filtration Grade Sponbonded Polypropylene Style Number 3301N. The dimensions of the stabilizing layer were approximately 40 mm×40 mm and the stabilizing layer was arranged in the center of the product.

Inventive Sample 5 was tested to determine the MCB value within the area defined by stabilizing layer and outside the area of the stabilizing layer, the MCB values are provided in the chart below.

|  | MCB (g) within Stabilizing Layer Area | MCB (g) outside Stabilizing Layer Area |
| --- | --- | --- |
| Inventive Sample 5 | 526 | 114 |

In view of the above absorbent articles according to the present invention provide the unique combination of a highly flexible, drapeable, absorbent article that has excellent fluid handling properties.

Applications of the absorbent article according to the present invention for sanitary and other health-care uses can be accomplished by any sanitary protection, incontinence, medical and absorbent methods and techniques as are presently or prospectively known to those skilled in the art. Thus, it is intended that the present application cover the modifications and variations of this invention provided that they come within the scope of the appended claims and their equivalents.

We claim:

1. An absorbent article comprising:
   a cover layer;
   a barrier layer;
   an absorbent system arranged between said cover layer and said barrier layer;
   wherein said absorbent article has a thickness of less than 2.5 mm;
   wherein the absorbent article has a first portion and a second portion, said second portion having an MCB that is greater than an MCB of said first portion; and
   wherein at least part of said first portion satisfies one of the following equations:

$AI > 2.37 - 0.77 \ln(BW/MCB)$, where BW/MCB is $\leq 5.9$; and $AI > 1.0$, where BW/MCB is $> 5.9$.

2. The absorbent article according to claim 1, wherein said absorbent article has a thickness of less than 2.0 mm.

3. The absorbent article according to claim 1, wherein said absorbent article has a thickness of less than 1.5 mm.

4. The absorbent article according claim 1, wherein said absorbent system includes superabsorbent material.

5. The absorbent article according to claim 4, wherein said absorbent system comprises a material including a mixture of cellulosic fibers and superabsorbent material.

6. The absorbent article according to claim 5, wherein said material contains from about 90% to about 40% cellulosic fibers and about 10% to about 40% SAP.

7. The absorbent article according to claim 6, wherein said material is embossed to have at least a first region and a second region.

8. The absorbent article according to claim 7, wherein said first region has a density greater than said second region.

9. The absorbent article according to claim 8, wherein said first region covers about 20% to about 60% of said of the surface area of the material and wherein said second region comprises between about 40% and about 80% of said material.

10. The absorbent article according to claim 9, wherein said first region has a density greater than 0.3 g/cc and said second region has a density in the range from about 0.07 to about 0.25 g/cc.

11. The absorbent article according to claim 10, wherein said material has a basis weight of about 50 to about 600 gsm.

12. The absorbent article according to claim 1, wherein said absorbent system is a material manufactured by an air-laying process.

13. The absorbent article according to claim 12, wherein said material comprises cellulosic fibers, binder material and nonbonding materials.

14. The absorbent article according to claim 13, wherein said material includes less than 50% cellulosic fibers, less than 20% binder material and greater than 30% non-bonding materials.

15. The absorbent article according to claim 14, wherein said material has a basis weight of about 50 gsm to about 600 gsm.

16. The absorbent article according to claim 1, wherein said absorbent system is substantially entirely SAP.

17. The absorbent article according to claim 16, wherein said SAP is present in an amount of at least 50 gsm.

18. The absorbent article according to claim 16, wherein said SAP is present in an amount of between about 100 gsm and about 150 gsm.

19. The absorbent article according to claim 16, wherein said SAP has an absorbency rate of at least 20 g/g after 1 minute.

20. The absorbent article according to claim 16, wherein said SAP has a total capacity of at least 40 g/g.

21. The absorbent article according to claim 16, wherein said SAP is secured to an internal surface of said barrier.

22. The absorbent article according to claim 21, wherein said SAP is secured to said internal surface of said barrier by adhesive.

23. The absorbent article according to claim 1, wherein the cover is a spunlace material including from about 10 to about 65 wt % rayon and from about 35 to about 90 wt % polyester.

24. The absorbent article according to claim 1, wherein at least a portion of said absorbent article has a BW/MCB ratio of at least 2.5.

25. The absorbent article according to claim 1, wherein at least a portion of said absorbent article has a BW/MCB ratio of at least 10.0.

26. The absorbent article according to claim 1, wherein at least a portion of said absorbent article has a BW/MCB ratio of at least 20.0.

27. The absorbent article according to claim 24, wherein said article has an AI of at least 1.71.

28. The absorbent article according to claim 25, wherein said article has an AI of at least 1.74.

29. The absorbent article according to claim 26, wherein said article has an AI of at least 1.5.

30. The absorbent article according to claim 26, wherein said article has an AI of at least 1.78.

31. The absorbent article according to claim 1, wherein said absorbent article is a sanitary napkin.

32. The absorbent article according to claim 1, wherein said absorbent article is a pantiliner.

33. The absorbent article according to claim 1, wherein said absorbent article is an incontinence device.

34. The absorbent article according to the claim 1, wherein said second portion has an MCB of at least 400 g.

35. The absorbent article according to claim 1, wherein said second portion is defined by a layer of material arranged between said cover layer and said barrier layer.

36. The absorbent article according to claim 35, wherein said material defining said second portion has a length that is less than a length of said absorbent system.

37. The absorbent article according to claim 36, wherein said material defining said second portion has a width that is equal to a width of said absorbent system.

38. The absorbent article according to claim 1, wherein at least a portion of said absorbent article has a BW/MCB ratio of at least 2.5.

39. The absorbent article according to claim 16, wherein said SAP has a gel blocking ratio of at least 0.50.

40. An absorbent article comprising:
a cover layer;
a barrier layer;
an absorbent system arranged between said cover layer and said barrier layer;
wherein said absorbent article has a thickness of less than 2.5 mm;
wherein the absorbent article has a first portion and a second portion, said second portion having an MCB that is greater than an MCB of said first portion;
wherein at least part of said first portion satisfies one of the following equations:

$AI > 2.37 - 0.77 \ln(BW/MCB)$, where BW/MCB is $\leq 5.9$;

$AI > 1.0$, where BW/MCB is $> 5.9$; and wherein said absorbent system consists of a layer of superabsorbent material arranged between said cover layer and said barrier layer, said layer of superabsorbent material having a basis weight between 100 gsm and 150 gsm.

* * * * *